United States Patent
Cassart et al.

(10) Patent No.: US 12,404,546 B2
(45) Date of Patent: Sep. 2, 2025

(54) DETECTION OF METHYLATION STATUS OF A DNA SAMPLE

(71) Applicant: DIAGENODE S.A., Seraing (BE)

(72) Inventors: Clément Cassart, Vaux-et-Borset (BE); Renaud Schoemans, Seraing (BE)

(73) Assignee: Diagenode S.A., Ougree (BE)

( * ) Notice: Subject to any disclaimer, the term of this patent is extended or adjusted under 35 U.S.C. 154(b) by 0 days.

(21) Appl. No.: 18/885,331

(22) Filed: Sep. 13, 2024

(65) Prior Publication Data

US 2025/0002987 A1 Jan. 2, 2025

Related U.S. Application Data

(63) Continuation of application No. PCT/IB2023/052012, filed on Mar. 3, 2023.

(60) Provisional application No. 63/320,053, filed on Mar. 15, 2022.

(51) Int. Cl.
*C12Q 1/6851* (2018.01)

(52) U.S. Cl.
CPC ................... *C12Q 1/6851* (2013.01)

(58) Field of Classification Search
None
See application file for complete search history.

(56) References Cited

U.S. PATENT DOCUMENTS

| | | | | |
|---|---|---|---|---|
| 2011/0166197 | A1* | 7/2011 | Darling | A61P 7/04 435/375 |
| 2018/0298447 | A1* | 10/2018 | Fleischhacker | C12Q 1/6886 |
| 2022/0177956 | A1* | 6/2022 | Frumkin | G01N 33/491 |

FOREIGN PATENT DOCUMENTS

| | | |
|---|---|---|
| WO | WO 2005/042704 A2 | 5/2005 |
| WO | WO 2011/109529 A1 | 9/2011 |
| WO | WO 2016/138105 A2 | 9/2016 |
| WO | WO 2017/043497 A1 | 3/2017 |
| WO | WO 2019/142193 A1 | 7/2019 |
| WO | WO 2020/188561 A1 | 9/2020 |
| WO | WO 2023/175434 A1 | 9/2023 |

OTHER PUBLICATIONS

Von Kanel et al. Quantitative 1-Step DNA Methylation Analysis with Native Genomic DNA as Template. Clinical Chemistry 56(7):1098-1106. (Year: 2010).*
Oakes et al. Evaluation of a Quantitative DNA Methylation Analysis Technique Using Methylation-Sensitive/Dependent Restriction Enzymes and Real-Time PCR Epigenetics 1(3):146-152. (Year: 2006).*
Gagnon et al. Quantitative DNA methylation analysis of laser capture microdissected formalin-fixed and paraffin-embedded tissues. Experimental and Molecular Pathology 88:184-189. (Year: 2010).*
Eads et al. MethyLight: a high-throughput assay to measure DNA methylation. Nucleic Acids Research 28(8):e32 (2000). (Year: 2000).*
Eads et al. Epigenetic Patterns in the Progression of Esophageal Adenocarcinoma. Cancer Research 61:3410-3418 (2001). (Year: 2001).*
Dillinger et al. Identification of tumor tissue-derived DNA methylation biomarkers for the detection and therapy response evaluation of metastatic castration resistant prostate cancer in liquid biopsies. Molecular Cancer 27:7 (2022). (Year: 2022).*
Dillinger Supplemental Information [online] Jan. 3, 2022 [retrieved on Apr. 23, 2025] retrieved from https://molecular-cancer.biomedcentral.com/articles/10.1186/s12943-021-01445-0#Sec8 (Year: 2022).*
PCT/IB2023/052012 International Search Report and Written Opinion mailed Jun. 19, 2023.
PCT/IB2023/052012 International Preliminary Report on Patentability mailed Sep. 10, 2024.

* cited by examiner

*Primary Examiner* — Samuel C Woolwine
(74) *Attorney, Agent, or Firm* — Jeffrey E. Landes; Alston & Bird LLP

(57) ABSTRACT

The invention provides methods for quantitative analysis of methylation content of a test sample. The method employs an internal control within the same test sample and an external control within a reference sample to reduce sources of random variability. The internal control corrects for variability arising from conducting separate amplifications as occurs in an external control, and the external control corrects for variability between amplification at different loci as occurs with the internal control. The steps for processing and analyzing the test sample can occur in a single reaction vessel facilitating automation of the assay. Information regarding methylation content generated by the methods can be used in diagnosing and treatment of disorders and for forensic purposes among other applications.

14 Claims, 3 Drawing Sheets

Specification includes a Sequence Listing.

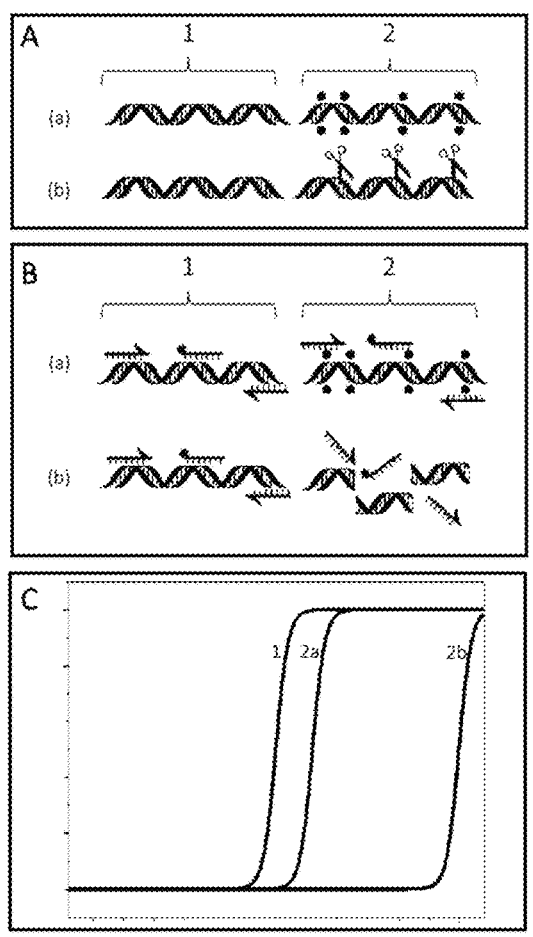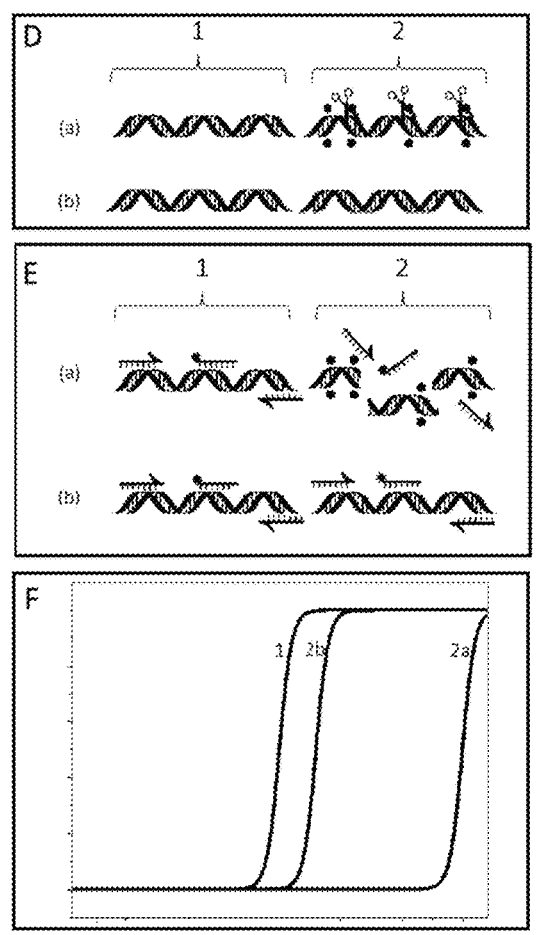
Figs. 1A-F

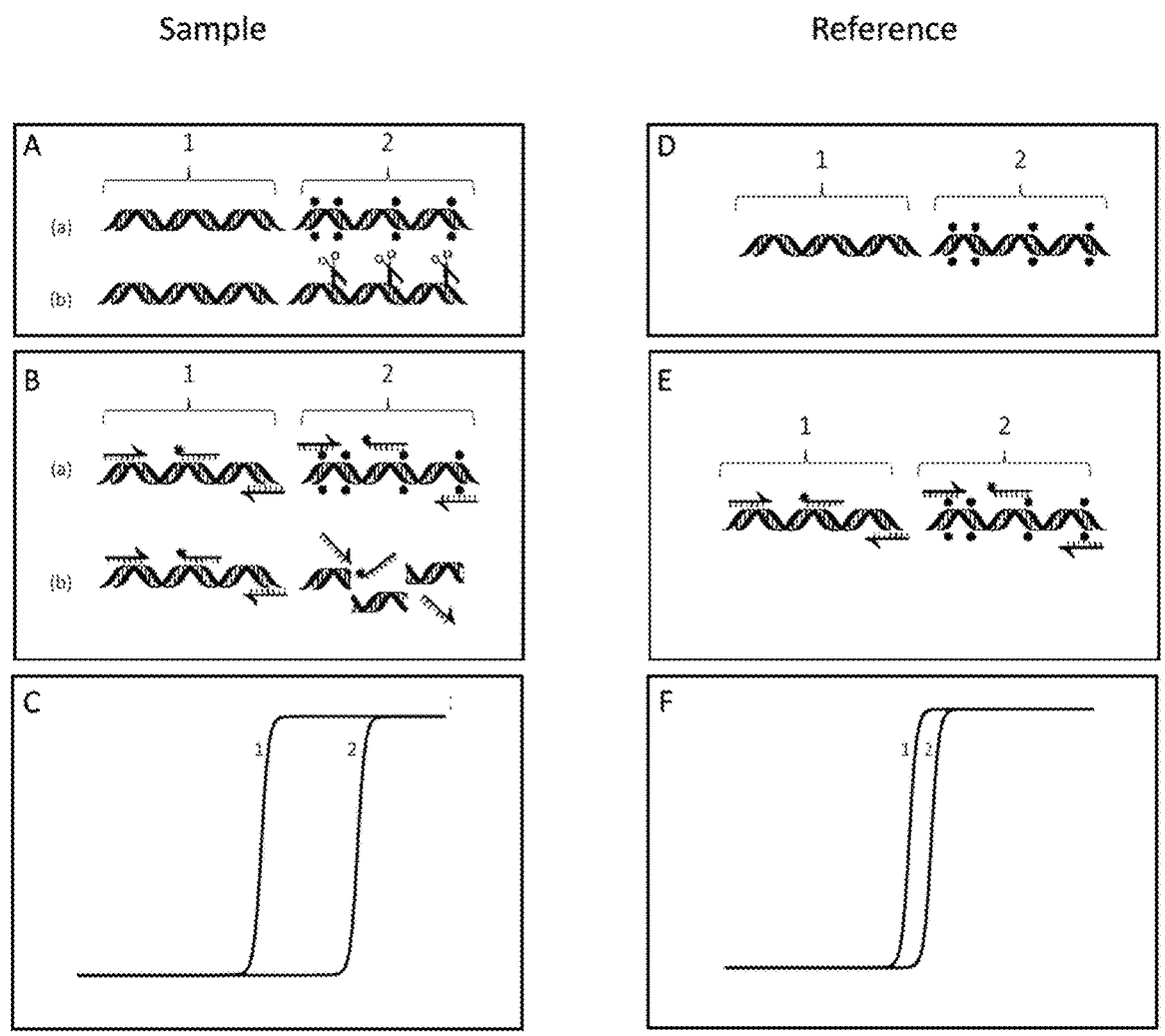
Figs. 2A-F

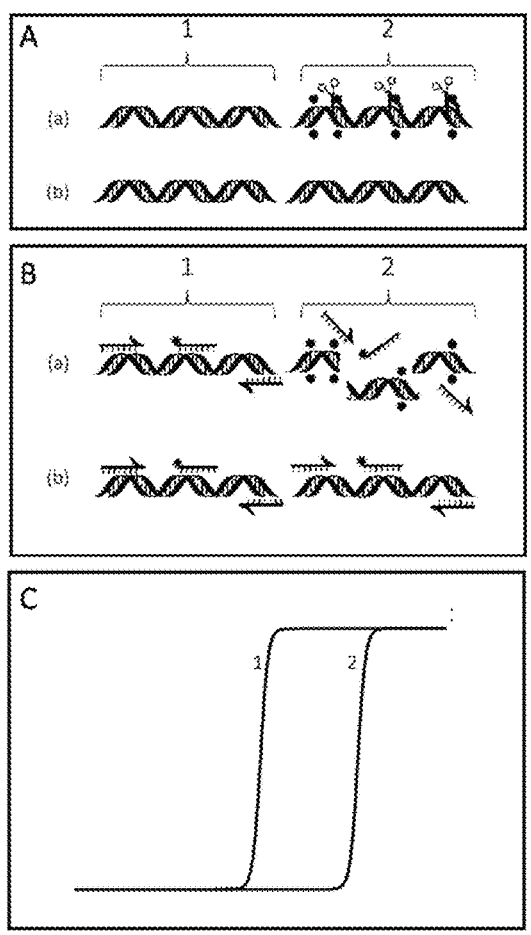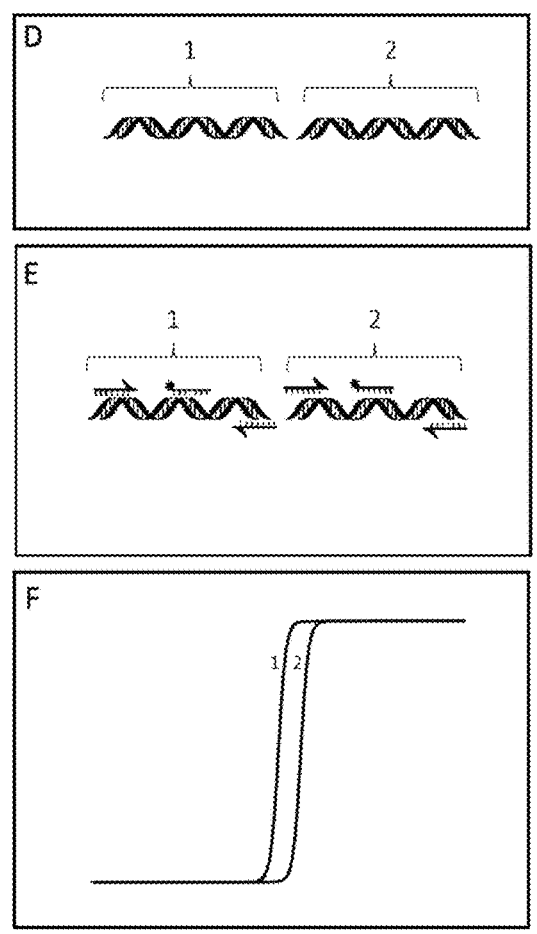
Figs. 3A-F

SEQUENCE LISTING

```
Sequence total quantity: 6
SEQ ID NO: 1             moltype = DNA  length = 17
FEATURE                  Location/Qualifiers
source                   1..17
                         mol_type = other DNA
                         organism = synthetic construct
SEQUENCE: 1
actggctttg gcagcag                                                    17

SEQ ID NO: 2             moltype = DNA  length = 23
FEATURE                  Location/Qualifiers
source                   1..23
                         mol_type = other DNA
                         organism = synthetic construct
SEQUENCE: 2
tgcagtggga ctttattcca tag                                             23

SEQ ID NO: 3             moltype = DNA  length = 24
FEATURE                  Location/Qualifiers
source                   1..24
                         mol_type = other DNA
                         organism = synthetic construct
SEQUENCE: 3
tgtcacagcc tttgccttcc tctt                                            24

SEQ ID NO: 4             moltype = DNA  length = 21
FEATURE                  Location/Qualifiers
source                   1..21
                         mol_type = other DNA
                         organism = synthetic construct
SEQUENCE: 4
ctacaacgtg gacactgaga g                                               21

SEQ ID NO: 5             moltype = DNA  length = 21
FEATURE                  Location/Qualifiers
source                   1..21
                         mol_type = other DNA
                         organism = synthetic construct
SEQUENCE: 5
cgcatcagtc caactctact c                                               21

SEQ ID NO: 6             moltype = DNA  length = 23
FEATURE                  Location/Qualifiers
source                   1..23
                         mol_type = other DNA
                         organism = synthetic construct
SEQUENCE: 6
acaacacgct gttcggctac tcg                                             23
```

DETECTION OF METHYLATION STATUS OF A DNA SAMPLE

CROSS REFERENCE TO RELATED APPLICATION

This application is a continuation of PCT/IB2023/052012 filed Mar. 3, 2023, which claims the benefit of U.S. Application No. 63/320,053 filed Mar. 15, 2022, incorporated by reference in its entirety for all purposes.

REFERENCE TO A SEQUENCE LISTING

The application includes an electronic sequence listing named 618759SEQLST.XML of 6,231 bytes, created Sep. 12, 2024, which is incorporated by reference in its entirety for all purposes.

TECHNOLOGICAL FIELD

The present invention is in the field of epigenetics and is related to a DNA methylation assessment method, in particular by digestion with methyl sensitive or dependent restriction enzymes and quantitative amplification.

BACKGROUND

DNA methylation has been recognized as being an important source of information in cancer detection, treatment choice and treatment success follow up. Further, the utility and applicability of methylation extends in other pathological conditions as well, such as metabolic diseases or neurological disorders.

Due to its wide scope of applications in human medicine, the use of DNA methylation in diagnostic routine is of high interest, but yet limited by the lack of laboratory compatible routine methods to enable its full potential. The traditional, state-of-the-art methods for DNA methylation analysis are in most cases lengthy and involve a large number of process steps, which renders automation of DNA methylation analysis difficult. The length of the analysis and lack of automation are slowing down bringing DNA methylation analysis to the forefront.

DNA methylation occurs in mammals on cytosines in CG motifs, particularly formation of 5-methylcytosine (5mC). Some endonucleases termed methylation-sensitive restriction enzymes cleave DNA only when the recognition site of such an enzyme is unmethylated. Conversely methylation-dependent restriction enzymes, cleave DNA only when there restriction site is methylated.

The most widespread method to characterize and quantify methylation of genes is by bisulfite conversion of C to T residues. The conversion can be detected by sequencing separate aliquots before and after the conversion. Alternatively bisulfite conversion can be detected by an amplification assay using primers designed to bind primer binding sites including residues subject to conversion, thereby distinguishing methylated or unmethylated DNA. However, because of the bisulfite conversion step, such methods are destructive, labor intensive and difficult to automate.

EP 2 292 795 by ORION Genomics reports detecting the presence of methylation at a locus within a DNA population comprising the steps of dividing the DNA population into at least two physically distinct portions, digesting the first portion with MSRE and quantifying by quantitative amplification the number of intact copies of the locus in the digested first portion, digesting the second portion with MDRE and quantifying by quantitative amplification the number of intact copies of the locus in the digested second portion, and determining the presence of methylation at the locus within the population of nucleic acids by comparing the number of intact copies of the locus in this digested first portion and in this digested second portion.

EP 2 542 698 by ZYMO RESEARCH reports detecting the prevalence of methylation of a DNA sequence in a sample by the use of a MSRE enzyme, a Hot-Start DNA polymerase and oligo nucleotide primers with a buffer formulated to facilitate activity of the MSRE and the DNA polymerase, and with no additional components during contacting, incubating, and amplification of the DNA sample. The reaction mixture comprises at least two MSRE with specificity to different DNA sequences. DNA methylation is measured by the change in cycle threshold (Ct) value compared to a standard obtained without addition of the MSRE enzyme.

The methods described in EP 2 292 795 and EP 2 542 698 both require separating a clinical sample in multiple fractions, to be contacted by different MS/DRE or to be left intact before PCR. EP 2 292 795 also presents the drawback that they are articulated in one or two main steps performed on the multiple fractions: a digestion step, followed by a PCR step. The consequent splitting of a sample requires human intervention and/or more complex automation systems, and consumes more sample DNA. These method do not correct for each target qPCR signal (Ct) calculation variability due to background noise or template DNA fragmentation state. Furthermore, the methods are not readily adaptable to samples containing single-stranded DNA, such as FFPE tissue. They are also not easily automated limiting their utility for processing clinical samples.

EP 2 510 124 by NUCLEIX discusses a method for characterizing methylation level of a DNA sample as similar to a reference DNA sample representative of a particular condition (e.g., disease or normal state). Following digestion with a MSRE enzyme or a MDRE enzyme, at least two genomic loci from the digested DNA are amplified, and he signal intensity of the amplification product of each locus is determined. Signal ratios between the amplified products signal intensities are calculated and the signal ratios to reference values of different types of reference sample associated with known conditions to determine which reference DNA sample the test sample most closely resembles. The method does not result in quantification of methylation levels and is not readily adaptable to samples containing single-stranded DNA, such as FFPE tissue.

SUMMARY OF THE CLAIMED INVENTION

The invention provides a method for determining methylation of a test DNA sample comprising:
 (a) digesting a test DNA sample with one or more methylation-sensitive restriction endonuclease(s) (MSRE) or with one or more methylation-dependent restriction endonuclease(s) (MDRE), resulting in a digested test DNA sample,
 (b) inactivating the endonuclease(s);
 (c) subjecting the digested test sample DNA to a quantitative amplification reaction with at least two primer pairs configured to amplify first and second loci of the test sample DNA, wherein the second locus includes one or more recognition sites for the enzymes used in step (a) and the first locus lack recognition sites for the enzyme(s) used in step (a);

(d) determining from the quantitative amplification reaction values representing amounts of intact first and second locus in the digested test sample DNA;

(e) obtaining values representing amounts of intact first and second locus in a digested reference sample DNA, which values were determined by:

(a') a reference DNA sample being digested with the one or more methylation-sensitive restriction endonuclease(s) (MSRE) or with the one or more methylation-dependent restriction endonuclease(s) (MDRE), resulting in a digested reference DNA sample, the reference DNA sample being a methylated reference DNA sample for the one or more MSRE's and the reference sample being an unmethylated reference sample for the one or more MDRE's.

(b') the endonuclease(s) being inactivated;

(c') the digested reference DNA sample being subjected to separate quantitative amplification reactions with the at least two primer pairs to amplify first and second loci of the reference sample DNA, wherein the second locus includes one or more recognition sites for the enzymes used in step (a) and the first locus lack recognition sites for the enzymes used in step (a); and (f) determining a value of methylation of the test DNA sample from the relative values of intact first and second locus in the digested test sample DNA normalized by the relative values of intact first and second locus in the digested reference DNA.

Optionally, steps (a'), (b') and (c') are performed contemporaneously with steps (a), (b) and (c). Optionally, the reference sample is a historical control and steps (a'), (b') and (c') are performed before steps (a), (b) and (c). Optionally, step (a) is performed with the one or more MSRE(s) and preferably fewer than 5% of molecules in the reference DNA sample are cleaved by the one or more MSRE's in locus 2. Optionally, step (a) is performed with the one or more MDRE(s) and the reference sample is an unmethylated control and preferably fewer than 5% of molecules in the reference DNA sample are cleaved by the one or more MDRE's in locus 2. Optionally, at least one recognition site for one of the enzyme(s) used in step (a) is methylated in the second locus of the reference DNA sample. Optionally, the method further comprises performing an in vitro methylation reaction on reference DNA to provide the reference DNA sample. Optionally, the method further comprises propagating reference DNA in a host incapable of methylating the reference DNA at recognition sites for the enzyme(s) used in step (a) in the second locus. Optionally, the method further comprises mutating the second locus of the reference sample to remove at least one methylation recognition site. Optionally, each recognition site of the enzyme(s) used in step (a) in the second locus of the reference DNA is unmethylated. Optionally, the values representing the intact first and second loci in the test sample DNA and reference sample DNA are Ct values. Optionally, the relative values are determined by calculating $\Delta Ct_{ts}$ as $Ct_{ts l2} - Ct_{ts l1}$ and $\Delta Ct_{rs}$ as $Ct_{rs l2} - Ct_{rs l1}$ and, wherein ts is test sample, rs is reference sample, l1 is the first locus and l2 is the second locus. Optionally, the normalization is performed by calculating $\Delta\Delta Ct$ as $\Delta Ct_{ts} - \Delta Ct_{rs}$, wherein $\Delta\Delta Ct$ is the value representing methylation of the test sample DNA. Optionally, the method further comprises calculating a methylation level as $100*(2^{-\Delta\Delta Ct})$ if step (a) is performed with MSRE(s) and the reference sample is a methylated control and $100*(1-2^{-\Delta\Delta Ct})$ if step (a) is performed with MDRE(s) and the reference sample is an unmethylated control. Optionally, the digesting step (a) has a duration of at least 30 seconds, preferably between 1 minute and 120 minutes, more preferably between 5 minutes and 60 minutes. Optionally, the endonuclease(s) inactivation step (b) comprises treating with heat. Optionally, the test DNA sample and/or the reference DNA sample includes enzyme(s) with non-specific endonuclease activity. Optionally, the test sample DNA and reference sample DNA are genomic, episomal, plasmid or cDNA DNA samples. Optionally, the method further comprises fragmenting the test DNA sample and/or the reference DNA sample before performing step (a). Optionally the method further comprises propagating the test DNA sample and/or the reference DNA sample in a cell before performing step (a). Optionally, the method further comprises adding the MSRE's and/or one or more MDRE's, and optionally, a restriction enzyme reaction mix to the test sample DNA and reference sample DNA before performing step (a).

Optionally, the test DNA sample and/or reference DNA sample comprise single-stranded DNA and the method further comprises adding a single-stranded DNase to the test DNA sample and/or reference DNA sample to digest the single-stranded DNA. Optionally, the test DNA sample and/or the reference DNA sample is a paraffin-embedded formalin-fixed sample.

Sometimes the method is performed twice, once with MSRE(s), and once with MDRE(s). optionally, the method further comprises separating the test sample DNA and/or reference sample DNA into two aliquots to use with MSRE(s) and MDRE(s) respectively.

Optionally, the method further comprises determining from the value of methylation of the test DNA sample that a subject providing the test DNA sample has a disorder, e.g., cancer.

Optionally the one or more MSRE is selected from AciI, HpaII, HinP1I and HpyCH4IV. Optionally, the one or more MDRE is selected from MspJI, LpnPI, FSpEI, SgeI, McrBC, McrA, or MrrA.

Optionally, in step (a') a second reference DNA sample as well as the reference sample are digested, wherein the reference sample and second reference sample are methylated and unmethylated control reference samples, with the one or more methylation-sensitive restriction endonuclease(s) (MSRE) and/or methylation dependent endonucleas(s) (MDRE) with the resulting in a second reference DNA sample, In step (c') the digested second reference DNA sample is subjected to a separate quantitative amplification reaction with the at least two primer pairs which determines values representing amounts of intact first and second locus in the digested second reference DNA sample; and step (f) comprises determining the value of methylation of the test DNA sample from the relative values of intact first and second locus in the digested test sample DNA normalized by the relative values of intact first and second locus in the digested reference DNA sample and the relative values of intact first and second locus in the second digested reference DNA sample.

Optionally, the relative values are determined by calculating $\Delta Ctts$ as $Cttsl2 - Cttsl1$, $\Delta Ctrs$ as $Ctrsl2 - Ctrsl1$ and $\Delta Ctrs2$ as $Ctrs2l1 - Ctrs2l2$, wherein ts is test sample, rs is reference sample, l1 is the first locus, l2 is the second locus and the superscript 2 indicates the second reference.

Optionally, the digesting and amplification steps are performed in the same vessel.

The invention further provides a kit for performing the method according to any one of the preceding claims, comprising one or more MSRE and/or one or more MDRE, a reference DNA sample, and instructions and/or a software for performing the method. Optionally, the kit comprises an MSRE, which is AciI, HpaII, HinP1I or HpyCH4IV. Optionally, the kit comprises an MDRE, which is MspJl, LpnPl, FSpEl, Sgel, McrBC, McrA, or MrrA.

The invention further provides a method for determining methylation of a test DNA sample, comprising:
(a) digesting a test DNA sample with one or more methylation-sensitive restriction endonuclease(s) (MSRE) or with one or more methylation-dependent restriction endonuclease(s) (MDRE), resulting in a digested test DNA sample,
(b) inactivating the endonuclease(s);
(c) subjecting the digested test sample DNA to a quantitative amplification reaction with at least two primer pairs configured to amplify first and second loci of the test sample DNA, wherein the second locus includes one or more recognition sites for the enzymes used in step (a) and the first locus lack recognition sites for the enzyme(s) used in step (a);
(d) determining from the quantitative amplification reaction values representing amounts of intact first and second locus in the digested test sample DNA;
(e) obtaining values representing amounts of intact first and second locus in a digested reference sample DNA, which values were determined by:
  (a') a reference DNA sample being digested with one or more methylation-sensitive restriction endonuclease(s) (MSRE) or with one or more methylation-dependent restriction endonuclease(s) (MDRE), resulting in a digested reference DNA sample, wherein the reference DNA sample is a methylated DNA reference sample for digestion by the one or more MSRE's such that preferably less than 5% of DNA molecules in the reference sample are cleaved in locus 2 by the one or more MSRE(s) and an unmethylated DNA reference sample for digestion by the one or more MDRE's such that preferably less than 5% of DNA molecules in the reference sample are cleaved in locus 2 by the one or more MDRE's;
  (b') the endonuclease(s) being inactivated;
  (c') the digested reference DNA sample being subjected to separate quantitative amplification reactions with the at least two primer pairs to amplify first and second loci of the reference sample DNA, wherein the second locus includes one or more recognition sites for the enzymes used in step (a) and the first locus lack recognition sites for the enzymes used in step (a); and
(f) calculating $\Delta$Ctts as Ctts12–Ctts1 and $\Delta$Ctrs as Ctrs12–Ctrs11 and, wherein ts is test sample, rs is reference sample, 11 is the first locus and 12 is the second locus;
(g) calculating $\Delta\Delta$Ct as $\Delta$Ctts–$\Delta$Ctrs, wherein $\Delta\Delta$Ct; and
(h) calculating a methylation level as $100*(2^{-\Delta\Delta Ct})$ if step (a) is performed with MSRE(s) and the reference sample is a methylated control and $100*(1-2^{-\Delta\Delta Ct})$ if step (a) is performed with MDRE(s) and the reference sample is an unmethylated control.

BRIEF DESCRIPTION OF THE FIGURES

FIGS. 1A-F represent schematically some exemplary principles of the present MS/DRE-qPCR detection methods. FIGS. 1A to C represent the MSRE-qPCR main steps, FIGS. 1D to F represent to MDRE-qPCR main steps. MSRE or MDRE enzymes are not graphically represented, but involved from the digestion step A or D, respectively. The DNA methyl groups are represented by hexagons and the enzymes endonuclease activity by scissors.

FIG. 1A represents the MSRE enzymes selective endonuclease activity which is only exerted on unmethylated DNA (b) while the methylated DNA (a) is protected. (a) and (b) represent different test samples. The input control DNA sequence (locus 1) does not contain any MSRE restriction recognition site and is therefore not subjected to DNA digestion, independently of its methylation status. The methylation marker of interest (locus 2) contains an MSRE restriction recognition site. In sample (a), locus 2 is methylated and in sample (b) locus 2 is not methylated. FIG. 1B represents the co-amplification by qPCR using separate dye labels of the input control (1) loci and of the methylation marker (2). FIG. 1C represents the amplification curves obtained after qPCR, fluorescence level (y-axis) by PCR cycle (x-axis). The Input control is PCR amplified independently of the methylation status and generates an early qPCR signal (1) in both test samples (a) and (b). The methylation marker generates an early qPCR signal, if methylated (2a) or a late qPCR signal, if unmethylated (2b). Of note, when the methylation marker is highly methylated, the associated qPCR signal (2a) can overlap with the input control locus signal (1) or even precedes it due to difference of PCR efficiency between the methylation marker and control locus assays, and when the methylation marker of interest is highly unmethylated, the associated qPCR signal (2b) can either still generates a late qPCR signal or none (beyond assay detection level). FIG. 1D represents the MDRE enzymes selective endonuclease activity which is only exerted on methylated DNA (a) while the unmethylated DNA (b) is protected. The input control DNA sequence (1) does not contain any MDRE restriction site and is therefore not subjected to DNA digestion independently of its methylation status. The methylation marker of interest (2) contains an MDRE restriction recognition site. FIG. 1E represents co-amplification by qPCR using separate dyes of the input control (1) loci and of the methylation marker of interest (2). FIG. 1F represents the amplification curves obtained after qPCR, fluorescence level (y-axis) by PCR cycle (x-axis). The Input control is PCR amplified independently of the methylation status and generates an early qPCR signal (1) in test samples (a) and (b). The methylation marker generates an early qPCR signal if unmethylated (2b) or a late qPCR signal if methylated (2a). Of note, when the methylation marker of interest is highly unmethylated, the associated qPCR signal (2b) can overlap with the input control locus signal (1) or even precede it due to difference of PCR efficiency between the methylation marker of interest and control locus assays, and when the methylation marker of interest is highly methylated, the associated qPCR signal (2a) can either still generates a late qPCR signal or none (beyond assay detection level).

FIGS. 2A-F represent schematically the main steps of DNA methylation quantification using the described method steps of the invention, more specifically the MSRE-qPCR detection method. FIGS. 2A to C represent the steps occurring on a DNA test sample material, FIGS. 2D to F represent the steps occurring on the reference material. MSRE enzymes are not graphically represented, but involved from the digestion step A and D. The DNA methyl groups are represented by hexagons and the enzymes endonuclease activity by scissors. (a) and (b) represent different DNA molecules within the same test sample with (a) being methylated in locus 2 and (b) being unmethylated in locus 2. In the FIGS. 2A and B, the logical approach explained in FIGS. 1A and B applies here. A moderate level of methylation for the methylation marker of interest was taken as example here, meaning both methylated and unmethylated forms of the methylation marker are part of the DNA sample material. FIG. 2C represents qPCR amplification results in an early qPCR signal (1) for the control input locus (locus 1) and a delayed qPCR signal (2) for the methylation marker of interest (locus 2), as a result of its partial MSRE digestion. From this DNA sample material qPCR data, the difference in signal between the methylation marker of interest and the input control loci is calculated as $\Delta Ct_{sample} = Ct_{marker} - Ct_{input\ control}$ to produce a raw assessment of the methylation marker's methylation level. In FIGS. 2D and E, the logical approach explained in FIGS. 1A and B applies. The reference material is virtually only composed of hypermethylated DNA, which protects the DNA from the specific MSRE endonuclease activity in FIG. 2D. FIG. 2F represents qPCR amplification results in early qPCR signals, for both the input control locus (1) and the methylation marker (2) of interest as a result of a lack of digestion. Differences in signal mainly stems from PCR efficiency difference between the two reactions, difference in non-specific restriction enzyme endonuclease activity or differences in background signal between the different dyes used in the co-amplification phase (2E). From the reference material qPCR data, the difference in signal (Ct) between the methylation marker and the input control loci is calculated as $\Delta Ct_{reference\ material} = Ct_{marker}\ (2) - Ct_{input\ control}\ (1)$. In FIGS. 2C and F, the differences in qPCR signals from both the DNA sample material and the reference material are combined to generate a normalized relative assessment of the methylation marker's methylation level in the DNA sample material, as $\Delta\Delta Ct = \Delta Ct_{sample} - \Delta Ct_{reference\ material}$. The percentage of methylated DNA is then calculated as $100*(2^{-\Delta\Delta Ct})$.

FIGS. 3A-F represents schematically the main steps of DNA methylation quantification using the described method steps of the invention, more specifically for the MDRE-qPCR detection method. FIGS. 3A to C represent the steps occurring on a DNA sample material, FIGS. 3D to F represent the steps occurring on the reference material. MDRE enzymes are not graphically represented but involved from the digestion step of FIGS. 3A and D. The DNA methyl groups are represented by hexagons and the enzymes endonuclease activity by scissors. In FIGS. 3A and B, the logical approach explained in FIGS. 1A and B applies here. A moderate level of unmethylation for the methylation marker was taken as example here, meaning both methylated and unmethylated forms of the methylation marker are part of the DNA sample material. FIG. 3C presents qPCR amplification results in an early qPCR signal (1) for the control input locus (locus 1) and a delayed qPCR signal (2) for the methylation marker of interest (locus 2), as a result of its partial MDRE digestion. From this DNA sample material qPCR data, the difference in signal (Ct) between the methylation marker of interest and the input control loci is calculated as $\Delta Ct_{sample} = Ct_{marker}\ (2) - Ct_{input\ control}\ (1)$ to produce a raw assessment of the methylation marker's unmethylation level. In FIGS. 3D and E, the logical approach explained in FIGS. 1A and B applies. The reference material is virtually only composed of unmethylated DNA, which protects the DNA from the specific MDRE endonuclease activity in 3D. FIG. 3F presents qPCR amplification results in early qPCR signals for both the input control locus (1) and the methylation marker (2) of interest as a result of a lack of digestion. Differences in signal mainly stems from PCR efficiency difference between the two reactions, difference in non-specific restriction enzyme endonuclease activity or differences in background signal between the different dyes used in the co-amplification phase (FIG. 3E). From the reference material qPCR data, the difference in signal between the methylation marker of interest and the input control loci is calculated as $\Delta Ct_{reference\ material} = Ct_{marker}\ (2) - Ct_{input\ control}\ (1)$. In FIGS. 3C and F, the differences in qPCR signals from both the DNA sample material and the reference material are combined to generate a normalized relative quantitation of the methylation marker's methylation level in the DNA sample material, as $\Delta\Delta Ct = \Delta Ct_{sample} - \Delta Ct_{reference\ material}$. The percentage of methylated DNA is then calculated as $100*(1 - 2^{-\Delta\Delta Ct})$.

DEFINITIONS

The present invention described herein uses several definitions set forth throughout the specification. Unless defined otherwise, all technical and scientific terms used herein generally have the same meaning as commonly understood by one of ordinary skill in the technical field of the invention "MSRE" stands for methylation-sensitive restriction enzyme and "MDRE" stands for methylation-dependent restriction enzyme.

In pairwise comparisons between two nucleic acid sequences, the nucleic acids are maximally aligned when the number of nucleobase matches is greatest. Percentage sequence identity can be defined as the number of matched nucleobases between aligned sequences divided by the number of nucleobases in one of the sequences (usually the known sequence if one sequence is known and the other is not). Extra nucleobases in an unknown sequence flanking the part of the unknown aligned with a known sequence are not scored.

A methylation site, such as C in CG, in a population of nucleic acid molecules can be methylated in one or more of the molecules and unmethylated in one or more molecules of the population. The percentage methylation for that site in the population is the number of molecules in which the site is methylated over the total number of molecules×100%. A locus in a nucleic acid can have multiple sites of methylation, each varying in whether the site is methylated throughout a population of nucleic acid molecules. The percentage methylation of the locus is the number of methylation sites in the locus bearing methylation summed over each of the population of molecules divided by the total number of methylation sites×the number of molecules× 100%. Percentages can likewise be calculated for a particular type of methylation such as 5-methylcytosine at a CG motifs. Percentages can likewise be calculated based on the proportion of recognition sites for a particular enzyme or enzymes within a defined locus that are methylated. For example, if a locus contains ten recognition sites for a particular MSRE and 5 of the sites are methylated in 25% of molecules in the population and the other 5 of the sites are methylated in 75% of molecules in the population, then the mean methylation level for the MSRE recognition sites in the locus is 50%. Methylation level can alternatively reflect whether a locus includes one or more MSRE or MDRE recognition sites subject to methylation without necessarily distinguishing whether multiple such sites are methylated in the same molecule. For example, if a locus includes two recognition sites for an MSRE, and 1 or 2 of the sites are methylated in 50% of molecules in a test DNA sample and 50% are unmethylated at both sites, then the methylation level can be scored at 50%. A relative level of methylation of a test sample relative to a reference sample of known methylation status can also be calculated from the formulae $100*(2^{-\Delta\Delta Ct})$ for MSRE and $100*(1-2^{-\Delta\Delta Ct})$ for MDRE's as discussed in more detail below. Methylation status of each of multiple methylation sites within a locus can be correlated or uncorrelated with one another. If the methylation level of a site or locus exceeds a mean methylation level and standard deviation of that site or locus in a control population (e.g., subjects not known to be suffering from a disease) then the methylation level can be described as hypermethylated. Likewise if the methylation status of a recognition site or locus is below a mean methylation level and standard deviation of that site or locus in a control population, the methylation level can be described as hypomethylated.

A "detection probe" is a nucleic acid or other molecule that binds specifically to a target DNA (e.g., an amplification product), and which binding results, directly or indirectly, in a detectable signal to indicate the presence of the target nucleic acid. Detection probes are used in quantitative PCR to provide a signal indicating an amount of an amplification product. A detection probe can be linked, directly or indirectly, to a label or detected with a label that binds specifically to the probe (e.g., Sambrook et al., Molecular Cloning, A Laboratory Manual, 2nd ed., Chapt. 10; U.S. Pat. No. 6,361,945, Becker et al.; U.S. Pat. No. 5,658,737, Nelson et al.; U.S. Pat. No. 5,656,207, Woodhead et al.; U.S. Pat. No. 5,547,842, Hogan et al.; U.S. Pat. No. 5,283,174, Arnold et al.; U.S. Pat. No. 4,581,333, Kourilsky et al.; U.S. Pat. No. 5,731,148, Becker et al.). For example, detection probes may include a non-nucleotide linker and a chemiluminescent label attached to the linker (U.S. Pat. Nos. 5,185,439, 5,585,481 and 5,639,604, Arnold et al.). Examples of detection probes include oligonucleotides of about 5 to 50 nucleotides in length having an attached label. Detection probes can have a nucleotide sequence that is of the same or opposite sense as a target sequence depending on the format of the assay. Some detection probes have an attached chemiluminescent marker, e.g., an acridinium ester (AE) compound (U.S. Pat. Nos. 5,185,439, 5,639,604, 5,585,481, and 5,656,744).

Detection probes and primers are complementary to a target nucleic acid. Complementarity of nucleic acids means that a nucleotide sequence in one strand of nucleic acid, due to orientation of its nucleobase groups, hydrogen bonds to another sequence on an opposing nucleic acid strand. The complementary bases typically are, in DNA, A with T and C with G, and, in RNA, C with G, and U with A. Complementarity can be perfect (i.e., exact) or substantial/sufficient. Perfect complementarity between two nucleic acids means that the two nucleic acids can form a duplex in which every base in the duplex is bonded to a complementary base by Watson-Crick pairing. "Substantial" or "sufficient" complementary means that a sequence in one strand is not completely and/or perfectly complementary to a sequence in an opposing strand, but that sufficient bonding occurs between bases on the two strands to form a stable hybrid complex in set of hybridization conditions (e.g., salt concentration and temperature). Such conditions can be predicted by using the sequences and standard mathematical calculations to predict the Tm of hybridized strands, or by empirical determination of Tm by using routine methods. Tm refers to the temperature at which a population of hybridization complexes formed between two nucleic acid strands are 50% denatured. At a temperature below the Tm, formation of a hybridization complex is favored, whereas at a temperature above the Tm, melting or separation of the strands in the hybridization complex is favored. Tm may be estimated for a nucleic acid having a known G+C content in an aqueous 1 M NaCl solution by using, e.g., Tm=81.5+0.41 (% G+C), although other known Tm computations take into account nucleic acid structural characteristics.

"Hybridization condition" refers to the cumulative environment in which one nucleic acid strand bonds to a second nucleic acid strand by complementary strand interactions and hydrogen bonding to produce a hybridization complex. Such conditions include the chemical components and their concentrations (e.g., salts, chelating agents, formamide) of an aqueous or organic solution containing the nucleic acids, and the temperature of the mixture. Other factors, such as the length of incubation time or reaction chamber dimensions may contribute to the environment (e.g., Sambrook et al., Molecular Cloning, A Laboratory Manual, 2.sup.nd ed., pp. 1.90-1.91, 9.47-9.51, 11.47-11.57 (Cold Spring Harbor Laboratory Press, Cold Spring Harbor, N.Y., 1989)).

An analysis of methylation is quantitative if it results in a value representative of the percentage methylation within a locus of a test sample. The value can be an absolute percentage with respect to methylation or a relative measure of methylation that can be compared with values of methylation of the same locus in other test or reference samples.

A restriction enzyme recognition site is the site on DNA recognized by the enzyme. A restriction enzyme cleavage site refers to the bond cleaved by the enzyme. A restriction enzyme cleavage site may or may not occur within the recognition enzyme site. Some MDRE's have a recognition site separate from the cleavage site.

A methylation site refers to a nucleotide that is or can be methylated. A methylation recognition site or motif refers to a nucleotide sequence, such as CpG, which is recognized by a methylating enzyme to methylate at least one nucleotide within the motif.

DETAILED DESCRIPTION

I. General

The invention provides methods for quantitative analysis of methylation content of a test sample. The method employs an internal control within the same test sample and an external control within a reference sample to reduce sources of random variability. The internal control corrects for variability arising from conducting separate amplifications as occurs in an external control, and the external control corrects for variability between amplification at different loci as occurs with the internal control. The combined use of these controls reduces potentially complicating factors, such as different ways of defining CT or other parameters, non-specific nuclease activity, and variation in amplification efficiency due to factors other than amount of intact template, such as genomic location of a locus. The steps for processing and analyzing the test sample can occur in a single reaction vessel, facilitating automation of the assay. Information regarding methylation content generated by the methods can be used in diagnosing and treatment of conditions and for forensic purposes among other applications. Exemplary embodiments are shown in FIGS. 1A-F, 2A-F and 3A-F.

II. Samples

A "sample" refers to any composition or mixture in which a target nucleic acid to be analyzed for methylation content is or may be present, including human patient samples, plant, fungus, eucaryotic, procaryotic, or animal materials, waste materials, materials for forensic analysis, environmental samples, and the like. A sample includes any tissue, cell, or extract derived from a living or dead organism which may contain a target nucleic acid, e.g., epidermis, hair, vaginal cells or secretions, feces, brain lung duodenum, stomach, peripheral blood, bone marrow, plasma, serum, biopsy tissue including lymph nodes, respiratory tissue or exudates, gastrointestinal tissue, urine, feces, semen, or other body fluids. Samples of particular interest are tissue samples (including body fluids) from a human or an animal having or suspected of having a condition. Other samples of interest include industrial samples, such as for water testing, food testing, contamination control, and the like. Samples can also be from plants such as roots, leaves, stem, roots, seeds, pollen, spore, caps and flowers. These samples can be fresh, frozen, preserved in a fixative such as an alcohol, formaldehyde, paraffin, or other fixatives known in the art, or diluted in a buffer.

Sample components may include target and non-target nucleic acids, and other materials such as salts, acids, bases, detergents, proteins, carbohydrates, lipids and other organic or inorganic materials.

A sample may or may not be subject of processing to purify or amplify a target nucleic acid before analyzing methylation as described below. Further processing can include simple dilution of a biological fluid with a lysing solution to more complex methods that are well known in the art (e.g., Su et al., J. Mol. Diagn. 2004, 6:101-107; Sambrook, J. et al., 1989, Molecular Cloning, A Laboratory Manual, 2nd ed., pp. 7.37-7.57; and U.S. Pat. Nos. 5,374,522, 5,386,024, 5,786,208, 5,837,452, and 6,551,778). A sample containing a target nucleic acid can be heated to inactivate enzymes in the sample (e.g., 90-100.degree. C. for 2-10 min, then rapidly cooling to 0-5.degree. C.).

III. Enzymes

The invention employs MSRE's and or MDRE's. Examples of MSRE's include AatlI, Acc65I, AccI, AciI, ACllAfel, AgcI, ApaI, ApaLI, AscI, AsiSI, Aval, AvalI, BacI, BanI, BbcI, BbeI, BceAI, BcgI, BfuCI, BglI, BmgBI, BsaBI, BssHlI, BssKI, BstAPI, BstBI, BstUI, BSTZ17I, Cac8I, ClaI, DpnI, DrdI, EaeI, EagI, EagI-HF, EciI, EcoRI, EcoRI-HF, FauII, Fnu4HI, FseI, FspI, HaeII, HgaI, HhaI, HincII, HinfI, HinP1I, HhaI, HpaI, HpaII, Hpy166ii, Hpy188iii, Hpy99I, HpyCH4IV, KasI, MluI, MmeI, MspA1I, MwoI, NaeI, NarI, NgoNIV, Nhe-HFI, NheI, N1aIV, NotI, NotI-HF, NruI, Nt.BbvCI, Nt.bsmAI, Nt.CviPII, PaeR7I, PleI, PmeI, Pm1I, PshAI, PspONMI, PvuI, RsaI, RsrII, SacII, Sa1I, Sa1I-HF, Sau3AI, Sau961, ScrFI, SfiI, SfoI, SgrAI, SmaI, SnaBI, TfiI, TscI, TseI, TspMI, ZraI and any combination thereof. Preferably, the MSRE is one or more of AciI, HpaII, HinP1I, HpyCH4IV or a mixture thereof.

Examples of MDRE's include MspJI, LpnPI, FSpEI, SgeI, McrBC, McrA, or MrrA, or any combination thereof. Preferably, the MDRE is FSpEI or SgeI or a combination thereof.

IV. Amplification

Although PCR is primarily referred to for purposes of illustration other amplification techniques that can be used include transcription-mediated amplification (TMA), ligase chain reaction (LCR), strand displacement amplification (SDA), and nucleic acid sequence based amplification (NASBA). Whereas PCR reverse transcribes RNA to DNA prior to amplification (e.g., RT-PCR), TMA and NASBA can directly amplify RNA.

Transcription mediated amplification (U.S. Pat. Nos. 5,480,784 and 5,399,491), commonly referred to as TMA, synthesizes multiple copies of a target nucleic acid sequence autocatalytically under conditions of substantially constant temperature, ionic strength, and pH in which multiple RNA copies of the target sequence autocatalytically generate additional copies. See, e.g., U.S. Pat. Nos. 5,399,491 and 5,824,518. In a variation described in U.S. Publ. No. 20060046265, TMA optionally incorporates the use of blocking moieties, terminating moieties, and other modifying moieties to improve TMA process sensitivity and accuracy.

Strand displacement amplification (Walker et al., *Proc. Natl. Acad. Sci. USA* 89:392-396 (1992); U.S. Pat. Nos. 5,270,184 and 5,455,166,), commonly referred to as SDA, uses cycles of annealing pairs of primer sequences to opposite strands of a target sequence, primer extension in the presence of a dNTPs to produce a duplex hemiphosphorothioated primer extension product, endonuclease-mediated nicking of a hemi-modified restriction endonuclease recognition site, and polymerase-mediated primer extension from the 3' end of the nick to displace an existing strand and produce a strand for the next round of primer annealing, nicking and strand displacement, resulting in geometric amplification of product. Thermophilic SDA (tSDA) uses thermophilic endonucleases and polymerases at higher temperatures in essentially the same method (EP Pat. No. 0 684 315).

The ligase chain reaction (Weiss, *Science* 254:1292 (1991) commonly referred to as LCR, uses two sets of complementary DNA oligonucleotides that hybridize to adjacent regions of the target nucleic acid. The DNA oligonucleotides are covalently linked by a DNA ligase in repeated cycles of thermal denaturation, hybridization and ligation to produce a detectable double-stranded ligated oligonucleotide product.

Other amplification methods include, for example: nucleic acid sequence based amplification (U.S. Pat. No. 5,130,238), commonly referred to as NASBA; one that uses an RNA replicase to amplify the probe molecule itself (Lizardi et al., *BioTechnol.* 6:1197 (1988, commonly referred to as Qß replicase; a transcription based amplification method (Kwoh et al., *Proc. Natl. Acad. Sci. USA* 86:1173 (1989)); and, self-sustained sequence replication (Guatelli et al., *Proc. Natl. Acad. Sci. USA* 87:1874 (1990). For further discussion of known amplification methods see Persing, "In Vitro Nucleic Acid Amplification Techniques" in *Diagnostic Medical Microbiology: Principles and Applications* (Persing et al., Eds.), pp. 51-87 (American Society for Microbiology, Washington, D.C. (1993)).

If an amplification technique other than PCR is used any amplification parameter related to the number of initial molecules of intact template can be used in place of Ct for PCR. Such parameters can be based on the rate of generation of amplification product, time to first emergence of detectable amplification product, or amount of amplification product.

V. Labels

A "label" refers to a molecular moiety that is detectable or produces a detectable response or signal directly or indirectly, e.g., by catalyzing a reaction that produces a detectable signal. Labels include luminescent moieties (such as fluorescent, bioluminescent, or chemiluminescent compounds), radioisotopes, members of specific binding pairs (e.g., biotin and avidin), enzyme or enzyme substrate, reactive groups, or chromophores, such as a dye or particle that results in detectable color. Exemplary labels include ethidium bromide staining, sybr green staining, silver staining and fluorophores.

VI. Automation and Computers

The present methods can be computer-implemented, such that steps other than wet chemistry steps, particularly calculating and data processing or transfer steps are carried out on a suitably programmed computer. The computer can be a stand-alone computer or can be coupled to other apparatus used in the present methods, such as a PCR thermocycler or other amplification apparatus. The computer can be a main frame, desktop, tablet, smart phone or the like. Coupling can be physical or virtual such as via internet connection. The present methods can be implemented in a computer program stored on computer-readable media, such as the hard drive of a standard computer. A computer program for analyzing a nucleic acid target can include one or more of the following codes: (a) code for receiving amplification parameters, such as Ct values, (b) code for calculating differences or ratios of such values between first and second loci of a test sample or a reference sample, (c) code for normalizing test sample values with reference sample values, and (d) code for calculating a methylation level. Such a computer program can also include code for calculating $\Delta Ct_{ts}$ as $Ct_{ts l2}-Ct_{ts l1}$ and $\Delta Ct_{rs}$ as $Ct_{rs l2}-Ct_{rs l1}$ and, wherein ts is test sample, rs is reference sample, l1 is the first locus and l2 is the second locus. The computer program can also include code for calculating $\Delta\Delta Ct$ as $\Delta Ct_{ts}-\Delta Ct_{rs}$, wherein $\Delta\Delta Ct$ is the value representing methylation of the second locus in test sample DNA. The computer program can also include code for calculating a methylation level as $100*(2-\Delta\Delta Ct)$ if step (a) is performed with MSRE(s) and $100*(1-2-\Delta\Delta Ct)$ if step (a) is performed with MDRE(s).

A computer program for analyzing a nucleic acid target can also include one or more of the following codes: code for receiving nucleic acid sequences first and second loci with the target and reference samples, and code for determining presence of recognition sites for MSRE's or MDRE's within such loci.

The present methods can be implemented in a system (e.g., a data processing system) for analyzing methylation content of a test DNA sample. The system can also include a processor, a system bus, a memory coupled to the system bus, wherein the processor is coupled to the system bus for one or more of the following: a) receiving amplification parameters, such as Ct values, (b) calculating differences or ratios of such values between first and second loci of a test sample or a reference sample, c) normalizing a test sample values with reference sample values and (d) calculating a methylation level of a locus.

Various steps of the present methods can utilize information and/or programs and generate results that are stored on computer-readable media (e.g., hard drive, auxiliary memory, external memory, server; database, portable memory device (e.g., CD-R, DVD, ZIP disk, flash memory cards), and the like. For example, information used for and results generated by the methods that can be stored on computer-readable media include Ct values and values determined from them, including methylation levels.

Any or all of the wet chemistry steps can be automated using commercial equipment for transfer of reagents, sample processing and extraction, mixing, incubating, thermocycling or other amplification and signal detection. Examples of equipment compatible with the methods include ROCHE LC480® and BioRad CFX96® thermocyclers, and Qiagen extraction Spin columns. Hologic's Panther Fusion® apparatus can be adapted for automating all the wet chemistry steps and performing numerous assays in parallel.

VII. Methylation Analysis

The present methods use endonuclease activity of one or more restriction enzymes, which are sensitive or dependent to the methylation status of cytosine(s) included in the recognition sites of the one or more enzymes (MRSE and MDRE's respectively).

A test DNA sample is analyzed in combination with a reference DNA sample. The test DNA sample comprises DNA at least in part of unknown methylation level, whereas the methylation level of the reference DNA sample is at least in part known, (i.e., more fully characterized for methylation level than the test sample as a result of the reference sample being prepared under conditions that result in methylation or absence of methylation and/or subject to prior analysis of methylation level). Knowledge of methylation level may be partial when it is known for one region of DNA molecule(s) in a sample but not others, or it is known qualitatively that methylation is present within a region but not quantitatively. The test DNA sample and reference DNA sample can be any type of DNA, for example, genomic DNA, episomal DNA, plasmid DNA or cDNA. The DNA can be obtained as a sample from an individual or other natural source, or from a cell line (e.g. HTC116 DKO cell line), or synthesized synthetically. The test sample and reference DNA sample can be the same type of DNA as each other (e.g., both genomic) or different (e.g., test sample complete genome, reference sample cloned fragment).

The various steps performed on test and reference samples can be performed in parallel, that is contemporaneously. That is, performance of corresponding individual steps on test and reference samples occur at overlapping times or at least the entire processing of the test and reference sample can overlap in time. Alternatively, the reference sample can be a historical control that serves for multiple test samples. A historical control on the reference sample is normally performed before processing of the test samples. A historical control can be performed by the same or different entity as processing of the test samples. Regardless of whether test and reference samples are processed contemporaneously or at different times, the different processing steps are preferably performed in the same sequence with the same reagents and conditions. For example, the same MSRE(s) or MDRE(s) are used under the same digestion conditions, the enzymes are inactivated under the same conditions, single-stranded DNase if used is used on both test and reference samples under the same conditions, and amplifications are performed with the same primer pair(s) and amplification conditions.

Test and reference samples can be subject to various processing steps before performing digestion with MSRE(s) or MDRE(s). Processing steps can include purification, separation from other nucleic acids, fragmentation, fractionation of DNA, conversion of RNA to cDNA by reverse transcriptase or removal of single-stranded DNA or RNA among others. The DNA can also be subject to amplification, for example, rolling circle-amplified DNA, such as EpiTect control DNA (QIAGEN).

If the test DNA sample or reference DNA sample contains single-stranded DNA as well as double-stranded DNA, the single-stranded DNA can be removed by digestion with a single-strand DNase. Examples of DNase with a high specificity for single-stranded DNA are described in Lehman et al., The Enzymes 14, 193-201 (1981) including *N. crassa*, *Aspergillus oryzae* and mung bean nucleases. Single-strand DNase digestions should occur before amplification but can occur before or after before digestion with MSRE(s) or MDRE(s). Single-stranded DNA does not digest with MSRE(s) or MDRE(s) but can amplify generating a background signal. Presence of single-stranded DNA can occur in samples which have been fixed (e.g., formalin fixed paraffin embedded samples), or which have been degraded. RNA in the test or reference sample can likewise be removed by RNA digestion.

The DNA in test and reference samples comprises first and second loci. The first and second loci in the reference DNA sample are corresponding sequences with the first and second loci in the test DNA sample. Corresponding sequences between test and reference DNA sample are identical to one another or have maximum identity among pairwise combinations of maximally aligned sequences from the test and reference samples. For example, if the first and second loci are genomic sequences, their start and stop points typically occur at the same genomic locations. The first and/or second locus in the reference sample can undergo mutagenesis to remove bacterial methylation recognition sites, such as Dcm.

Each locus has a length amenable to amplification from a pair of forward and reverse primers configured to amplify the locus (e.g., 50-5000 base pairs). Preferably the lengths of the first and second loci are the same, or similar (e.g., +/−10%). The second locus includes one or more restriction recognition site(s) for one or more MSRE and/or MDRE enzymes. Preferably, the second locus includes 1-20, 1-10, 1-5, 2-20, 2-10, 2-5 of 3 restriction recognition sites for MSRE's and/or 1-20, 1-10, 1-5, 2-20, 2-10, 2-5 of 3 restriction recognition sites for MDRE's. The first locus is selected to lack restriction recognition sites for at least one and preferably all of the MSRE's and MDRE's which have sites present in the second locus. The first and second loci is each amplifiable from a different pair of forward and reverse primers. Typically the same pair of forward and reverse primers is used for amplifying the first locus in both test and reference samples and likewise the second locus.

The test DNA sample and reference DNA sample(s) are contacted with one or more MSRE and/or MDRE enzymes forming digested test DNA samples and digested reference DNA sample(s) respectively. Typically test and reference samples are contacted in separate vessels. Typically, the method uses MSRE(s) or MDRE(s) but not both in the same digestion. However, the method can be performed in two cycles using MSRE(s) in one cycle and MDRE(s) in another cycle on separate aliquots of test sample.

The reference DNA sample serves as a control of known methylation status. The control can be a methylated control, in which some or all of the reference DNA and particularly a second locus, as further described below is hypermethylated, or an unmethylated control in which all or some of the reference DNA, and particularly the second locus, is hypomethylated. Hypermethylated DNA can be prepared by e.g., performing an in vitro DNA methylation reaction on DNA to be used as the test sample. In vitro methylation can be performed with commercially available methyltransferases available from companies, such as NEB. One such enzyme is CpG methyltransferase (m.SssI). In humans, the family of DNMT enzymes includes de novo DNA methyltransferases DNMT3A and DNMT3B, and the maintenance DNA methyltransferase DNMT1. When used as a methylated control, preferably, each recognition site for an MSRE or MDRE to be used in the assay in the second locus of the reference DNA sample is methylated on at least 75, 90, 95% or 100% of molecules in the reference DNA sample. A methylation level of over 95% is preferred meaning that fewer than 5% of molecules in the sample will be cleaved within locus 2 by an MSRE. Hypomethylated DNA can be obtained by propagating DNA in a host incapable of methylation or having impaired methylation capacity. An example of such a strain is *E. coli* hsdSB (rB- mB-), which is defective for both methylation and restriction. Alternatively, the reference material sequence is altered at bacterial DNA cytosine methyltransferase (Dcm) recognition site(s) to prevent activity of such enzymes. For example bacterial recognition sites CCAGG and CCTGG can be mutated to CAAGG or CATGG respectively. Bacterial methylation recognition sites are different than mammalian recognition sites (e.g., CpG). Thus, bacterial methylation recognition sites can be mutated without affecting mammalian recognition sites. When used as an unmethylated control, preferably each methylation recognition site for an MSRE or MDRE to be used in the assay in the second locus of the reference DNA sample is methylated on less than 25, 20, 5% or more preferably zero of molecules in the reference DNA sample. A methylation level of less than 5% means that less than 5% of DNA molecules in a reference sample are cleaved in locus 2 by an MDRE.

Methylation level of a reference sample can be determined by comparing Ct with and without digestion by an MSRE or MDRE. The delta Ct between the locus 2 non-digested and digested conditions reflects the % of methylation. The methylation % is derived from: a single $\Delta Ct$ calculated as $\Delta Ct = Ct(locus\ 2\ digested)\ Ct\ locus\ 2\ not\ digested$, then $100*(2^{-\Delta Ct})$ for MSRE and $100*(1-2^{-\Delta Ct})$ for MDRE. Alternatively, the calculation can performed from comparison of locus 1 and 2, each with and without digestion by an MSRE or MDRE. $\Delta Ct1 = Ct\ locus2\ digested - Ct\ locus1\ digested$. $\Delta Ct2 = Ct\ locus2\ not\ digested - Ct\ locus1\ not\ digested$. $\Delta\Delta Ct = \Delta Ct1 - \Delta Ct2$. Then methylation percent is calculated from $100*(2^{-\Delta\Delta Ct})$ for MSRE and $100*(1-2^{-\Delta\Delta Ct})$ for MDRE Optionally, a comparison can be performed with both methylated and unmethylated controls.

For an MRSE digestion, a methylated control is provided as a control for amplification and for calculation of $\Delta Ct_{rs}$. An unmethylated control can also be provided as a control for MRSE digestion. This control is not necessary for calculating $\Delta Ct_{rs}$. For MDRE digestion, the reverse is the case. An unmethylated control is provided as a control for amplification and calculation of $\Delta Ct_{rs}$ and a methylated control is provided as a control for MDRE digestion. The methylated control is not needed for calculation of $\Delta Ct_{rs}$.

If the same test DNA sample is to be analyzed with both MSRE's and MDRE's, then the test DNA sample can be split into two aliquots one for digestion with MSRE(s) and the other for digestion with MDRE(s). The two aliquots can be digested and amplified in parallel in separate vessels.

The digesting step typically has a duration of at least 30 seconds, preferably between 1 minute and 120 minutes, such as between 2 minutes and 90 minutes, more preferably between 5 minutes and 60 minutes, such as between 10 minutes and 50 minutes. The second amplification locus can contain one or more recognition site for an MSRE or MDRE. Regardless of whether 1 or more than 1 recognition site is present digestion by an MSRE or MDRE preferably proceeds to completion. Therefore, if a locus 2 contains one or more recognition sites for an MSRE and at least one of the sites is unmethylated in a molecule, then the molecule is cleaved by the MSRE and not subject to amplification. If a molecule has a locus 2 in which no MSRE recognition site is unmethylated, then locus 2 is not cleaved by an MSRE and is subject to amplification. If a locus 2 contains one or more recognition sites for an MDRE and at least one is methylated in a molecule, then the molecule is cleaved and not subject to amplification. If a locus 2 contains one or more recognition sites for an MDRE and none is methylated, then locus 2 is not cleaved by an MDRE and is subject to amplification.

After the digestion step, the MSRE or MDRE endonuclease(s) are inactivated such as by heat treatment (e.g., 70-100° C.). The digested samples are then subject to a quantitative amplification reaction with first and second pairs of primers configured to amplify the first and second loci described above. The first and second loci for the test sample can be coamplified in the same reaction; likewise the first and second loci for the reference sample can be coamplified in another reaction. Amplification products of the first and second loci can be distinguished using differential labels among other methods. The amplification reaction used for test and reference DNA samples is preferably a quantitative amplification in which a signal is generated and detected in real time corresponding to the amount of amplification product generated. The amount of amplification product generated is in turn dependent on the amount of intact and therefore amplifiable first and second loci in the test and reference DNA samples. The amount of intact second locus depends on whether and how much digestion took place with MSRE and MDRE's in the prior step. The amount of intact first and second locus can also depend on whether contaminating non-specific nucleases are present but such distortions can be reduced by use of test and reference samples equally likely to be contaminated.

Digestion with MSRE(s) or MDRE(s) and amplification can be carried out in the same vessel using the same reaction mix or in different vessels with the reaction mix customized for the respective reactions. Use of the same vessel with reactions occurring sequentially subject to temperature control increases the automation potential of the method and therefore the applicability in clinical routine. If the reactions are performed in separate vessels an aliquot of digested DNA is transferred from a first vessel after MSRE or MDRE digestion to a second vessel for amplification.

Quantitative amplification can generate a value representative of the amount of amplification product or rate at which amplification product is generated, which is in turn representative of an amount of intact (undigested by MSRE or MDRE's) first or second locus in a sample. A commonly used value for this purpose is the Ct value, which represents the number of amplification cycles for a signal representing amplification product to emerge above background level. The Ct value is representative of the amount of template (i.e., first or second locus) giving rise to the amplification product, a higher Ct value indicating less intact first or second locus in a sample. Methylation level of the second locus from the test sample is determined from the relative values of intact first and second locus in the digested test sample DNA (e.g., represented by Ct values) normalized by the relative values of intact first and second locus in the digested reference DNA (e.g., also represented by Ct values). For example, the relative values of Ct for the first and second loci of the test DNA sample can be expressed by calculating $\Delta Ct_{ts}$ as $Ct_{ts/2}-Ct_{ts/1}$. Likewise the relative values of Ct for the first and second loci of the reference DNA sample can be expressed by calculating $\Delta Ct_{rs}$ as $Ct_{rs/2}-Ct_{rs/1}$ and, wherein ts is test sample, rs is reference sample, l2 is the second locus and l1 is the first locus. The relative values of the test sample can then be normalized against the relative values of the reference sample by calculating $\Delta\Delta Ct$ as $\Delta Ct_{ts}-\Delta Ct_{rs}$, wherein $\Delta\Delta Ct$ is the value representing methylation of the test sample DNA. For MSRE-digested samples, the percentage of methylated DNA can be calculated as $100*(2^{-\Delta\Delta Ct})$. For MDRE-digested samples, the percentage of methylated DNA was calculated as $100*(1-2^{-\Delta\Delta Ct})$. The relative Ct values of the first and second locus can alternatively be compared as a ratio or percentage. Normalization can alternatively be performed by comparing relative values of the test DNA sample and reference DNA sample as a ratio or percentage.

If both methylated and unmethylated reference DNA samples are included then $\Delta Ct_{rs}=Ct_{rs/2}-Ct_{rs/1}$ can be calculated for both reference samples.

Although the method has been described for one pair of first and second loci, it can expanded to a plurality of such pairs to generate methylation status of a plurality of second loci. The pairs of first and second loci can be analyzed in multiplex in the same vessel or in separate vessels or a combination thereof. If analyzed in the same vessel different amplification products can be distinguished using loci specific probes, optionally with different labels. The number of pairs of first and second loci analyzed can be at least 2, 5, 10, 20, 50, 100 or 1000.

As the method of the invention only uses one fraction of the test sample, it simplifies the technology and reduces the amount of human intervention and DNA required to run the analysis. The use of a single DNA fraction adds the benefit of using a single reference point (first locus) for all methylation markers to explore (second loci), instead of having to repeat twice, the amplification for each methylation marker to explore (amplify each marker in a fraction contacted by MS/DRE and in a fraction non-contacted), hence reducing the assay complexity and cost.

In addition, the use of a locus containing no MS/DRE restriction recognition sites is more robust than using a locus of given methylation status, which could be by nature prone to inter-individual variation Furthermore, the method of the invention, through the use of a single step protocol decreases the amount of human intervention, greatly eases the automation of the procedure and for each target reduce qPCR signal (Ct) calculation variability due to background noise, which is taken into account through the use of the $\Delta\Delta Ct$ calculation, resulting in a more robust DNA methylation assessment.

VIII. Applications

In normal cells, DNA methylation regulates gene expression and stable gene silencing. DNA methyltransferases are responsible for establishing and maintenance of methylation pattern. Hypermethylation particularly within promoter regions can result in gene suppression and thus hyperproliferative disorders, particularly cancer. For example, hypermethylation of tumor suppressor genes reduces their expression and increases potential for cancers. On the other hand, global hypomethylation, inducing genomic instability, also contributes to cell transformation. DNA methylation also regulates expression of noncoding RNAs such as microRNAs that play role in tumor suppression. Examples of cancers associated with abnormal methylation levels include colon, breast, liver, bladder, Wilms, ovarian, esophageal, prostate, and bone cancers, hepatocellular carcinoma, glioblastoma, breast cancer, squamous cell lung cancer, thyroid carcinoma, and leukemia. Abnormal methylation levels are also associated with disorders, such as obesity, diabetes, and cardiovascular and neurodegenerative disorders, inflammation, auto-immune disorder, metabolic disorder, infection, degenerative disease, hormonal imbalance, neurodevelopment disorder, such as centromeric instability and facial abnormalities and Rett syndrome (see e.g., Jin et al., Genes Dis. 5(1): 1-8 (2018)).

Detection of methylation showing significant variation from those in normal control subjects can thus provide an indication of presence of disorders, particularly cancer, and response of such disorders to treatment. Methylation levels can also be used to characterize normal physiological conditions.

Methylation levels also vary with age, gender and tissue type (e.g., blood, saliva, semen, vaginal material) in different human individuals. Analysis of methylation levels can therefore be used for forensic purposes in characterizing tissue type, age and gender of forensic test samples. Methylation levels can also provide a basis to distinguish samples from monozygotic twins having an identical primary DNA sequence.

Methylation levels can also be used to characterize prenatal conditions, such as Prader-Willi syndrome, Angelman syndrome, Beckwith-Wiedmann syndrome, fragile X syndrome, Russell-Silver syndrome, transient neonatal diabetes mellitus, Albright hereditary osteodystrophy, McCune-Albright syndrome, familial nonchromaffin paraganglioma, the maternal and paternal UPD14 syndrome, and to distinguish fetal and maternal DNA.

IX. Kits

The invention also provides a kit including any of the disclosed reagents for performing any of the methods disclosed herein. Such a kit can include one or more MSRE or one or more MDRE, one more reference DNA samples of at least partly known methylation level, and optionally instructions and/or a software for performing the method and obtaining the DNA methylation level of a test DNA sample material.

EXAMPLES

Samples

Two reference material DNA samples were provided in the form of fragments cloned into plasmids. The first control DNA sample was a methylated control DNA sample, i.e. a non-digested control for MSRE-qPCR. The second control DNA sample was a non-methylated control DNA sample, i.e. a non-digested control for MDRE-qPCR prepared with a hypomethylation: deficient bacterial strain or altered Dcm recognition sites.

Sample Preparation

DNA Extraction

DNA is extracted from other cellular materials in test and reference DNA samples by conventional methods. A preferred solution is the technology of Qubit systems for dsDNA quantification (see thermofisher.com/be/en/home/industrial/spectroscopy-elemental-isotope-analysis/molecular-spectroscopy/fluorometers/qubit.html) The Qubit dsDNA HS assay utilizes a target-specific dye that emits fluorescence when bound to dsDNA. Unlike UV spectroscopy, which can overestimate sample concentration due to contaminants in a sample, the Qubit Fluorometer together with the Qubit dsDNA HS assay does not measure salts, nucleotides, or RNA that may be present.

The concentration of double-stranded DNA sample was 0.05 ng/µL. The following protocol was built with a DNA concentration is ≥5 ng/µL MSRE-Digestion A MSRE digestion mix as described in Table 1 was prepared.

TABLE 1

| Reagent | Digestion concentration |
| --- | --- |
| Digestion buffer | 1X |
| For each MSRE enzyme | 0.1-10 U |
| H$_2$O | up to 20 µL |
| MSRE mix | 20 µL |
| DNA sample | 0.1-250 ng |
| MSRE reaction | 24 µL |

The tubes were inverted several times and were spun down.

20 µL of MSRE mix was dispensed into 0.2 mL PCR-strip tubes. 5 µL of test DNA sample was added in the corresponding tube. A reference DNA sample digest was set up in parallel. The strip-tubes were inverted several times and were spun down. The samples were incubated at 37° C. for 1 hour, after which the enzymes were inactivated by heating the mixture to 80° C. for 20 minutes.

MDRE-Digestion

A MDRE digestion mix as described in Table 2 below was prepared.

TABLE 2

| Reagent | Digestion concentration |
| --- | --- |
| Digestion buffer | 1X |
| For each MDRE enzyme | 0.1-10 U |
| H$_2$O | Up to 20 µL |
| MDRE mix | 20 µL |
| DNA sample | 0.1-250 ng |
| MDRE reaction | 24 µL |

The tubes were inverted several times and were spun down.

20 µL of MDRE mix was dispensed into 0.2 mL PCR-strip tubes. 5 µL of test DNA sample was added in the corresponding tube. A digestion of a reference DNA sample was set up in parallel. The strip-tubes were inverted several times and were spun down. The samples were incubated at 37° C. for 1 hour, after which the enzymes were inactivated by heating the mixture to 80° C. for 20 minutes.

Preferred ssDNase Treatment Specific to Formalin Fixed and Embedded Paraffin (FFPE) Fixation A ssDNAse mix as described in Table 3 below was prepared. The ssDNAse mix is the ssDNAse+digestion buffer+H$_2$O from Table 3.

TABLE 3

| Reagent | Digestion concentration |
| --- | --- |
| Digestion buffer | 1x |
| ssDNAse | 0.1-100 U |
| H$_2$O | Up to 5 µL |
| ssDNAse mix total | 5 µL |

The tube was inverted several times and were spun down. The ssDNAse mix was dispensed into a strip-tube. 5 µL of ssDNase mix was added in each strip-tube. The strip-tubes were inverted several times and were spun down. The samples were incubated at 37° C. for 15 minutes, after which the enzymes were inactivated by heating the mixture to 80° C. for 20 minutes.

qPCR

4 µL of digested sample was added to 20 µL of qPCR MasterMix, as described in Table 4 below.

TABLE 4

| Reagent | PCR concentration |
| --- | --- |
| H$_2$O | NA |
| PCR buffer | 1x |
| Primer probe mix locus 1 (label 1 = Cy5) | 1x |
| Primer probe mix locus 2 (label 2 = FAM) | 1x |
| Digested sample | NA |
| PCR reaction | 24.0 |

The primers and probes were as follows:

| Oligo name | SEQ ID NO: | Sequence 5'→3' | 5' mod | 3' mod |
| --- | --- | --- | --- | --- |
| Locus 1 forward | 1 | ACTGGCTTTGGCAGCAG | N/A | N/A |
| Locus 1 reverse | 2 | TGCAGTGGGACTTTATTCCATAG | N/A | N/A |
| Locus 1 probe | 3 | TGTCACAGCCTTTGCCTTCCTCTT | FAM | BHQ1 |
| Locus 2 forward | 4 | CTACAACGTGGACACTGAGAG | N/A | N/A |
| Locus 2 reverse | 5 | CGCATCAGTCCAACTCTACTC | N/A | N/A |
| Locus 2 probe | 6 | ACAACACGCTGTTCGGCTACTCG | Cy5 | BHQ3 |

The PCR plate was sealed and centrifuged for 1 minute at 1500 rpm. qPCR was run for 2 minutes at 95° C. and 45 times the sequence of 15 seconds at 95° C. and 45 seconds at 60° C. Acquisition in different fluorophore channels (Fluorescein (FAM) and Cy5) was performed.

Data Analysis

The Ct value (threshold cycle value in qPCR) was extracted for each PCR well, in particular 1 Ct in label 1 (FAM) channel (locus 2) and 1 Ct in label 2 (Cy5) channel (locus 1).

For each test sample, by target marker, $\Delta Ct_{sample} = Ct_{locus\ 2}$ (FAM)$-Ct_{locus\ 1}$ (Cy5) was calculated.

For the reference material DNA sample, by target marker, $\Delta Ct_{reference} = Ct_{locus\ 2}$ (FAM)$-Ct_{locus\ 1}$ (Cy5) was calculated. The reference material DNA sample is methylated DNA for MSRE-digested samples and non-methylated DNA for MDRE-digested samples.

For each sample, $\Delta\Delta Ct = \Delta Ct_{sample} - \Delta Ct_{reference}$ was calculated.

For MSRE-digested samples, the percentage of methylated DNA was calculated as $100*(2^{-\Delta\Delta Ct})$.

For MDRE-digested samples, the percentage of methylated DNA was calculated as $100*(1-2^{-\Delta\Delta Ct})$.

Single Step MS/DRE-qPCR Protocol

DNA was extracted and 4 µL of sample DNA was added to 20 µL of MS/DRE-qPCR MasterMix as described in table 5 below.

TABLE 5

| Reagent | Reaction concentration |
| --- | --- |
| H$_2$O | NA |
| Digestion/PCR buffer 2X (comprising dNTPs, MgCl$_2$, Taq DNA polymerase) | 1X |

TABLE 5-continued

| Reagent | Reaction concentration |
| --- | --- |
| For each MSRE enzyme or MDRE enzyme | 0.1-10 U |
| Primers and probe "input control" | 0.01-1 µM |
| Primer and probe "target gene(s)" (for each target) | 0.01-1 µM |
| DNA sample | NA |
| One-step reaction | 24 µL |

The PCR plate was sealed and centrifuged for 1 minute at 1500 rpm. MS/DRE-qPCR was run as follows:
a. 10 minutes at 37° C.
b. 2 minutes at 95° C., and
c. 45 times 15 seconds at 95° C. and 45 seconds at 60° C.

Acquisition was performed in appropriate channels, and the data was analyzed as described above.

Only one patient sample fraction, contacted by enzymes through the use of a no cut site control.

Use of reference material also contacted with MSRE/MDRE enzymes to increase DNA methylation assessment precision and robustness.

Optionally, run with all reagent contained in a single buffer for the MSRE/MDRE digestion and qPCR phases These commercial qPCR buffers are compatible with the "single step" MS/DRE-qPCR used in the invention. Such specific buffer composition is not crucial for compatibility with MS/DRE digestion, MSRE or MDRE enzymes, primers, probes, dNTPS; and Taq polymerase).

Optionally, the ssDNAse digestion for the analysis of DNA containing large amounts of single strand, is for example formalin-fixed paraffin-embedded (FFPE) tissue samples, but is not limited to.

All publications, patents and patent applications, accession numbers, websites and the like mentioned in this specification are incorporated by reference to the same extent as if each individual publication, patent or patent application was so individually denoted. To the extent more different content is associated with an accession number or other reference at different times, the content in effect as of the effective filing date of this application is meant. The effective filing date is the date of the earliest priority application disclosing the accession number in question. Unless otherwise apparent from the context any element, embodiment, step, feature or aspect of the invention can be performed in combination with any other.

What is claimed is:

1. A method for determining methylation of a test DNA sample comprising:
   (a) digesting a test DNA sample with one or more methylation-sensitive restriction endonuclease(s) (MSRE), resulting in a digested test DNA sample,
   (b) inactivating the endonuclease(s);
   (c) subjecting the digested test sample DNA to a quantitative amplification reaction with at least two primer pairs configured to amplify first and second loci of the test sample DNA, wherein the second locus includes one or more recognition sites for the enzyme(s) used in step (a) and the first locus lack recognition sites for the enzyme(s) used in step (a);
   (d) determining from the quantitative amplification reaction values representing amounts of intact first and second locus in the digested test sample DNA;
   (e) obtaining values representing amounts of intact first and second locus in a digested reference sample DNA prepared by an in vitro methylation reaction on reference DNA to provide the reference DNA sample, which values were determined by:
   (a') a reference DNA sample being digested with the one or more methylation-sensitive restriction endonuclease(s) (MSRE), resulting in a digested reference DNA sample, the reference DNA sample being a methylated reference DNA sample;
   (b') the endonuclease(s) being inactivated; and
   (c') the digested reference DNA sample being subjected to separate quantitative amplification reactions with the at least two primer pairs to amplify first and second loci of the reference sample DNA, wherein the second locus includes one or more recognition sites for the enzymes used in step (a) and the first locus lack recognition sites for the enzymes used in step (a); and
   (f) determining a value of methylation of the test DNA sample from the relative values of intact first and second locus in the digested test sample DNA normalized by the relative values of intact first and second locus in the digested reference DNA, wherein the relative values are determined by calculating $\Delta Ct_{ts}$ as $Ct_{ts,l2} - Ct_{ts,l1}$ and $\Delta Ct_{rs}$ as $Ct_{rs,l2} - Ct_{rs,l1}$, wherein ts is the test sample, rs is the reference sample, l1 is the first locus and l2 is the second locus and the normalization is performed by calculating ΔΔCt as ΔCtts−ΔCtrs, wherein ΔΔCt is the value representing methylation of the test sample DNA.

2. The method of claim 1, wherein steps (a'), (b') and (c') are performed contemporaneously with steps (a), (b) and (c).

3. The method of claim 1, wherein the reference sample is a historical control and steps (a'), (b') and (c') are performed before steps (a), (b) and (c).

4. The method of claim 1, wherein fewer than 5% of molecules in the reference DNA sample are cleaved by the one or more MSRE's in locus 2.

5. The method of claim 1, wherein at least one recognition site for one of the enzyme(s) used in step (a) is methylated in the second locus of the reference DNA sample.

6. The method of claim 1, further comprising calculating a methylation level as $100*(2^{-\Delta\Delta Ct})$.

7. The method of claim 1, wherein the test DNA sample and/or the reference DNA sample includes enzyme(s) with non-specific endonuclease activity.

8. The method of claim 1, wherein the test sample DNA and reference sample DNA are genomic, episomal, plasmid or cDNA DNA samples.

9. The method of claim 1, further comprising fragmenting the test DNA sample and/or the reference DNA sample before performing step (a).

10. The method of claim 1, wherein the test DNA sample and/or reference DNA sample comprises single-stranded DNA and the method further comprises adding a single-stranded DNase to the test DNA sample and/or reference DNA sample to digest the single-stranded DNA.

11. The method of claim 1, wherein the test DNA sample and/or the reference DNA sample is a paraffin embedded formalin fixed sample.

12. The method of claim 1, further comprising determining from the value of methylation of the test DNA sample that a subject providing the test DNA sample has a disorder.

13. The method of claim 1, wherein the one or more MSRE is selected from AciI, HpaII, HinPII and HpyCH4IV.

14. The method of claim 1, wherein the digesting and amplification steps are performed in the same vessel.

* * * * *